United States Patent
Park et al.

(10) Patent No.: US 7,901,670 B2
(45) Date of Patent: *Mar. 8, 2011

(54) PROCESS FOR PURIFYING INTERFERON BETA

(75) Inventors: Ji Sook Park, Seoul (KR); Jong Sang Chung, Seoul (KR); Min Ji Baek, Yongin (KR); Jee Won Ahn, Seoul (KR); Ki Wan Kim, Seoul (KR); Hyung Ki Park, Seoul (KR); Dong Eok Lee, Seoul (KR); Myung Suk Oh, Suwon (KR)

(73) Assignee: CJ Cheiljedang Corporation, Seoul (KR)

( * ) Notice: Subject to any disclaimer, the term of this patent is extended or adjusted under 35 U.S.C. 154(b) by 716 days.

This patent is subject to a terminal disclaimer.

(21) Appl. No.: 10/581,597

(22) PCT Filed: Dec. 4, 2004

(86) PCT No.: PCT/KR2004/003180
§ 371 (c)(1),
(2), (4) Date: Jan. 9, 2007

(87) PCT Pub. No.: WO2005/054289
PCT Pub. Date: Jun. 16, 2005

(65) Prior Publication Data
US 2007/0123697 A1 May 31, 2007

(30) Foreign Application Priority Data
Dec. 4, 2003 (KR) .................. 10-2003-0087553

(51) Int. Cl.
*A61K 38/21* (2006.01)
*C07K 14/00* (2006.01)
*A23J 1/00* (2006.01)

(52) U.S. Cl. ......... 424/85.6; 530/351; 530/412; 530/413

(58) Field of Classification Search .................. None
See application file for complete search history.

(56) References Cited

U.S. PATENT DOCUMENTS

| | | | |
|---|---|---|---|
| 4,257,938 A | 3/1981 | Hosoi et al. | |
| 4,278,661 A | 7/1981 | Knight, Jr. | |
| 4,289,689 A | 9/1981 | Friesen et al. | |
| 4,359,389 A | 11/1982 | Heine | |
| 4,483,849 A | 11/1984 | Carter et al. | |
| 4,541,952 A | 9/1985 | Hosoi et al. | |
| 4,658,017 A | 4/1987 | Dembinski et al. | |
| 4,808,523 A | 2/1989 | Revel et al. | |
| 4,966,843 A | 10/1990 | McCormick et al. | |
| 5,066,786 A | 11/1991 | Protasi et al. | |
| 5,244,655 A | 9/1993 | Viscomi et al. | |
| 5,376,567 A | 12/1994 | McCormick et al. | |
| 5,795,779 A | 8/1998 | McCormick et al. | |
| 2003/0170206 A1 | 9/2003 | Rasmussen | |

FOREIGN PATENT DOCUMENTS

EP 0446850 A2 9/1991

OTHER PUBLICATIONS

Millipore Catalog citation for YM-10 ultrafiltration membranes: http://www.millipore.com/catalogue/itemdetail.do?id=13622, Feb. 2009.*
William Carter, et al., "Production, Purification and Clinical Application of Human Fibroblast Interferon", Pharmac. Ther., 1980, pp. 359-377, vol. 8.
M. Karpusas, et al., "The structure of human interferon-beta: implications for activity", Cellular and Molecular Life Sciences, 1998, pp. 1203-1216, vol. 54.
Sidney Pestka, et al., "Interferons and Their Actions", Annual Review Biochem., 1987, pp. 727-777, Annual Reviews Inc.
Hans Strander, et al., "Production of Interferon by Human Leukocytes in Vitro", Ann. Med. exp. Fenn., 1966, pp. 265-273, vol. 44.
T. Taniguchi, et al., "The nucleotide sequence of human fibroblast interferon cDNA", Gene, 1980, pp. 11-15, vol. 10.
Charles Weissmann, et al., "The Interferon Genes", Progress in Nucleic Acid Research and Molecular Biology, 1986, pp. 251-300, vol. 33, Academic Press, Inc.
E. Frederick Wheelock, "Interferon-Like Virus-Inhibitor Induced in Human Leukocytes by Phytohemagglutinin", Science, Jul. 16, 1965, pp. 310-311, vol. 149.
Chinese First Office Action issued on Mar. 14, 2008 with English translation, 7 pages.
European Office Action issued in EP 04 808 311.7, dated Jan. 30, 2009, 4 pages.
Japanese Office Action issued in JP Appln. No. 2006-542506 dated May 8, 2009, 3 pages.

* cited by examiner

*Primary Examiner* — Robert Landsman
*Assistant Examiner* — Bruce D Hissong
(74) *Attorney, Agent, or Firm* — Rothwell, Figg, Ernst & Manbeck, pc

(57) ABSTRACT

Provided is a process for purifying human interferon beta from a recombinant human interferon beta-containing culture comprising performing affinity chromatography and cation exchange chromatography, wherein the affinity chromatography includes: adsorbing the interferon beta-containing culture to an equilibrated affinity chromatography column, followed by washing with an equilibration buffer solution; washing the column with a washing buffer solution A of pH 6.5-7.5 containing 30-60 wt % of propylene glycol and a washing buffer solution B of pH 6.5-7.5 containing 10-30 wt % of propylene glycol and 1-2M NaCl; and eluting a human interferon beta-containing fraction with a buffer solution of pH 6.5-7.5 containing 40-60 wt % of propylene glycol and 1-2M NaCl.

4 Claims, 2 Drawing Sheets

PROCESS FOR PURIFYING INTERFERON BETA

CROSS REFERENCE TO RELATED APPLICATION

This application is a 35 U.S.C. §371 National Phase Entry Application from PCT/KR2004/003180, filed Dec. 4, 2004, and designating the United States.

BACKGROUND OF THE INVENTION

1. Field of Invention

The present invention relates to a process for purifying a human interferon beta from a recombinant human interferon beta-containing culture using affinity chromatography and cation exchange chromatography.

2. Description of the Related Art

Interferons in a broad meaning are extracellular messengers mediating reactivity of hosts and evolutionally conserved protein families that are released in a relatively small size from cells. Interferons are released from interferon-producing cells in response to stimulation by viruses, double-stranded RNAs, various microorganisms, or cytokines such as TNF or IL1, and then bind to surfaces of neighboring cells with interferon receptors. Thereafter, interferons induce synthesis of various proteins so that reactivity and homeostasis of hosts are maintained by consecutive signaling in the cells. Therefore, interferons act as antiviral, antiproliferative, and immune signaling proteins in the bodies and have direct anti-proliferation effects on cancer cells, and thus, have received much attention as therapeutic agents [Postka S., Langer J. A. and Zoon K. C. (1987) Interferons and their actions, Annu. Rev. Biochem. 56:727-777].

Interferons belong to the class of helical, physiologically active substances. According to physicochemical characteristics and functionalities, there are two classes of interferons: type 1 and 2. Interferon-alpha, -beta, -tau, and -epsilon are members of the type 1 interferon [Weissman C. and Weber H. (1986) The Interferon genes, Prog. Nucleic Acid Res. Mol. Biol. 33:251-300] and interferon gamma is a member of the type 2 interferon. Among them, interferon betas belonging to the type 1 interferon are proteins that exhibit species specificity. Interferon betas are also called as fibroblast interferons considering their sources and as pH2-stable interferons considering biological characteristics. Interferon betas bind to the same receptors of cell surfaces, together with interferon alphas belonging to the type 1 interferon, and then induce transcription of antiviral factors in response to a consecutive cell signaling system.

Interferon betas are glycoproteins (about 20% sugar moiety) with a molecular mass of about 20 kDa and single-chain proteins consisting of 166 amino acids. One N-glycosylation site is known to play a role in increasing material stability or solubility as physicochemical functions, rather than participating in biological activity or antigenicity [Karpusas M., Whytty A., Runkel L., and Hochman P. The structure of human interferon-β: implications for activity CMLS, 54:1203-1216 1998].

Advance in genetic recombination technology enabled determination of the amino acid sequence of human interferon beta and cloning and expression of human interferon beta in E. coli [Taniguchi, Gene 10:11-15, 1980]. Furthermore, expression of interferon beta in Chinese hamster ovary (CHO) cells was also reported [U.S. Pat. No. 4,966,843, U.S. Pat. No. 5,376,567, and U.S. Pat. No. 5,795,779].

Currently, interferon betas are manufactured by gene recombination technology and commercially available under the trade name of Betaseron®, Avonex®, and Rebif®. Recombinant interferon betas are known to be effective in delaying the progression of multiple sclerosis in patients with the signs of the disease and relieving the pains of the disease. Furthermore, recombinant interferon betas are widely used as therapeutic agents for multiple sclerosis, and at the same time are effective in nonspecific regulation of human immune response, immune response to viral infection, and anti-proliferation of cancer cells.

Currently available purification technologies of recombinant interferon betas expressed in CHO cells involve 3-5 purification procedures including primary purification by affinity chromatography (U.S. Pat. No. 4,278,661, U.S. Pat. No. 4,289,689, U.S. Pat. No. 4,541,952, U.S. Pat. No. 4,808,523, etc.), metal-chelate chromatography (U.S. Pat. No. 4,257,938, U.S. Pat. No. 4,359,389, U.S. Pat. No. 4,541,952, U.S. Pat. No. 5,244,655, etc.), CPG (controlled pore glass) chromatography (U.S. Pat. No. 4,359,389, U.S. Pat. No. 5,066,786, U.S. Pat. No. 5,244,655, etc.), or Concanavalin A chromatography (U.S. Pat. No. 4,289,689, U.S. Pat. No. 4,658,017, etc.) followed by cation exchange chromatography and reversed-phase chromatography.

In the above-described common purification technologies, metal-chelate chromatography may cause environmental contamination due to use of heavy metal. CPG or Concanavalin A chromatography has poor purification specificity. That is, Concanavalin A chromatography based on selective binding with many sugar-chain proteins contained in a CHO cell culture exhibits low specificity. A CPG column allows separation by molecular size after binding with a protein. However, separation efficiency and purity of interferon betas are lower than those by affinity chromatography (e.g., Blue Sepharose column chromatography).

Furthermore, common purification technologies by affinity chromatography involve washing and elution with ethylene glycol using a monoclonal antibody and/or a dye-resin. However, affinity chromatography using a monoclonal antibody separately requires the removal of the nonglycosylated form of interferon beta, which renders mass production difficult. In particular, ethylene glycol used in washing and elution is very toxic in the body, which restricts actual purification application.

Meanwhile, U.S. Pat. No. 4,483,849 discloses a process for purifying and stabilizing interferon beta using propylene glycol, instead of toxic ethylene glycol, by affinity chromatography. The process disclosed in this patent document includes applying an interferon-containing culture to a dye-affinity column such as equilibrated Affi-Gel Blue, washing the column with a 1.0M NaCl/PO$_4$ buffer solution and a 1.0M NaCl/PO$_4$ buffer solution containing 40% propylene glycol, and eluting interferon with 50% propylene glycol. Even though the process of this patent document involves column washing and elution, a desired final product peak and an impurity peak coexist, thereby lowering purity.

SUMMARY OF THE INVENTION

The present invention provides a process for purifying interferon beta, which includes recovering a high-purity primary purification product of interferon beta by enhanced affinity chromatography using nontoxic propylene glycol followed by cation exchange chromatography.

Therefore, the present invention provides a process for purifying human interferon beta from a recombinant human interferon beta-containing culture comprising performing affinity chromatography and cation exchange chromatography, which includes washing and elution with a specific buffer solution.

According to an aspect of the present invention, there is provided a process for purifying human interferon beta from a recombinant human interferon beta-containing culture comprising performing affinity chromatography and cation exchange chromatography, wherein the affinity chromatography includes: adsorbing the interferon beta-containing culture to an equilibrated affinity chromatography column, followed by washing with an equilibration buffer solution; washing the column with a washing buffer solution A of pH 6.5-7.5 containing 30-60 wt % of propylene glycol and a washing buffer solution B of pH 6.5-7.5 containing 10-30 wt % of propylene glycol and 1-2M NaCl; and eluting a human interferon beta-containing fraction with a buffer solution of pH 6.5-7.5 containing 40-60 wt % of propylene glycol and 1-2M NaCl.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
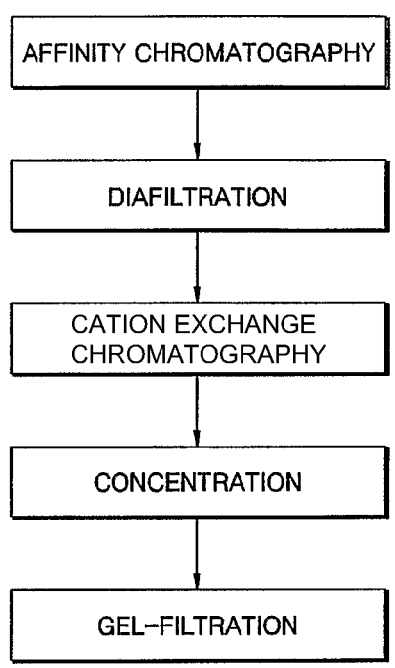
FIG. 1 is a flowchart illustrating a purification process of the present invention.

According to an aspect of the present invention, there is provided a process for purifying human interferon beta from a recombinant human interferon beta-containing culture comprising performing affinity chromatography and cation exchange chromatography, wherein the affinity chromatography includes: adsorbing the interferon beta-containing culture to an equilibrated affinity chromatography column, followed by washing with an equilibration buffer solution; washing the column with a washing buffer solution A of pH 6.5-7.5 containing 30-60 wt % of propylene glycol and a washing buffer solution B of pH 6.5-7.5 containing 10-30 wt % of propylene glycol and 1-2M NaCl; and eluting a human interferon beta-containing fraction with a buffer solution of pH 6.5-7.5 containing 40-60 wt % of propylene glycol and 1-2M NaCl.

In the purification process of the present invention, non-limiting examples of the recombinant human interferon beta-containing culture used as a sample include interferon beta-producing cells and strains. For example, the recombinant human interferon beta-containing culture may be a culture obtained by a known method disclosed in Carter and Horoszewicz, Pharm. Ther. 8, 359-377, 1980; Strander and Cantell, Ann. Med. Exp. Fenn. 44, 265-273, 1966; Wheelock, Science, 149, 310-311, 1965, and the like. Preferably, the recombinant human interferon beta-containing culture is a serum-free culture derived from recombinant human interferon beta-producing Chinese hamster ovary (CHO) cells.

In the purification process of the present invention, the affinity chromatography column used in the affinity chromatography may be a common dye-affinity column, for example a column (e.g., XK-50 column, Amersham biosciences, Sweden) packed with Blue-Sepharose 6 (Amersham biosciences, Sweden) or an Affi-Gel Blue column (Bio-Rad, America). The equilibration buffer solution for the affinity chromatography column may be a sodium phosphate-EDTA buffer solution (about pH 7.2). The affinity chromatography column may be equilibrated with 3 column volumes (CV) of the equilibration buffer solution, for example at a linear velocity of about 15-30 cm/hr.

In the purification process of the present invention, the affinity chromatography includes adsorbing the interferon beta-containing culture to the equilibrated affinity chromatography column and removing a nonspecifically bound protein by washing with the equilibration buffer solution.

The affinity chromatography also include multi-step washing, i.e., washing the column with a washing buffer solution A of pH 6.5-7.5 containing 30-60 wt % of propylene glycol and with a washing buffer solution B of pH 6.5-7.5 containing 10-30 wt % of propylene glycol and 1-2M NaCl. Preferably, the affinity chromatography further includes washing with a washing buffer solution C of pH 6.5-7.5 containing 1-2M NaCl. Preferably, each washing is performed with 2-4 CV of each buffer solution.

In the purification process of the present invention, there is no limitation on use sequence of the washing buffer solutions. That is, the washing may be performed using the washing buffer solution A and then the washing buffer solution B or using the washing buffer solution B and then the washing buffer solution A. Further, the washing may be performed using the washing buffer solution A, the washing buffer solution C, and then the washing buffer solution B, or using the washing buffer solution B, the washing buffer solution C, and then the washing buffer solution A. The washing with the washing buffer solution A effectively removes impurities with high hydrophobicity, the washing with the washing buffer solution C removes hydrophilic impurities, and the washing with the washing buffer solution B removes impurity proteins.

Interferon beta recovery may be performed by eluting a human interferon beta-containing fraction with a buffer solution of pH 6.5-7.5 containing 40-60 wt % of propylene glycol, preferably 50 wt %, and 1-2M NaCl.

Preferably, each buffer solution used in the washing or elution may be a sodium phosphate buffer solution or a potassium phosphate buffer solution.

In the purification process of the present invention, the washing with a buffer solution containing about 50% propylene glycol enables efficient removal of impurity peaks, which is in contrast to the process disclosed in U.S. Pat. No. 4,483,849 in which washing and elution are performed with a graded propylene glycol concentration gradient.

In the purification process of the present invention, the above-described affinity chromatography is followed by cation exchange chromatography. Preferably, prior to performing the cation exchange chromatography, an eluted solution from the affinity chromatography undergoes diafiltration with an ultrafiltration membrane of the molecular weight cut-off of 10,000. By the diafiltration, interferon beta with relatively high salt concentration can be adjusted to an appropriate salt concentration.

The cation exchange chromatography is performed as follows: a sample obtained by the diafiltration is loaded on a column and then a human interferon beta-containing fraction is eluted at pH 5-7 by a concentration gradient of NaCl. In detail, interferon beta-containing fractions are eluted by a linear concentration gradient from a sodium phosphate buffer solution (pH 5-7), which is an equilibration buffer solution, to a NaCl-containing sodium phosphate buffer solution (pH 5-7).

A column for the cation exchange chromatography may be CM-Sepharose FF (Amersham biosciences, Sweden) column (XK-50, 150 ml CV, Amersham biosciences, Sweden) and may be equilibrated with about 3 CV of a sodium phosphate buffer solution at a flow rate of 5 ml/mn. In the cation exchange chromatography, the sample obtained by the diafiltration is allowed to flow through the equilibrated column at an appropriate flow rate and eluted by a linear salt concentration gradient of a NaCl-containing sodium phosphate buffer solution (about 12 CV). As a result, interferon beta with no sugar chains is removed and interferon beta with a sugar chain is selectively obtained.

An interferon beta-containing fraction obtained by the cation exchange chromatography may be further subjected to replacement with a fresh buffer solution. The replacement with a fresh buffer solution may be performed by gel-filtration or concentration and diafiltration.

For example, in the case of performing gel-filtration, the interferon beta-containing fraction obtained by the cation exchange chromatography is concentrated to, for example about 200-1,000 μg/ml, dialyzed with 10-50 mM sodium acetate buffer solution (pH 3.5-5.5), and loaded on a gel-filtration chromatography column (e.g., Sephacryl S-200, Amersham biosciences) equilibrated with 10-50 mM, preferably 20 mM sodium acetate buffer solution (pH 3.5-5.5). 10-50 mM sodium acetate buffer solution (pH 3.5-5.5) is then allowed to flow through the column at an appropriate flow rate, thereby resulting in solution replacement for target proteins and separation and removal of polymers.

A flowchart illustrating the purification process of the present invention is shown in FIG. 1.

Hereinafter, the present invention will be described more specifically by Examples. However, the following Examples are provided only for illustrations and thus the present invention is not limited to or by them.

Example 1

Affinity Chromatography 350 ml of Blue-Sepharose 6 (Amersham biosciences, Sweden) was packed in a XK-50 column (Amersham biosciences, Sweden) to make an affinity chromatography column. A 20 mM sodium phosphate buffer solution containing 1 mM EDTA was allowed to sufficiently flow through the column to equilibrate the column. Then, 25 L of a Chinese hamster ovary (CHO) cell serum-free culture containing interferon beta was allowed to flow through the column at a flow rate of 5-10 ml/min and then the column was washed with about 3 column volumes (CV) of an equilibration buffer solution.

About 3 CV of a 20 mM sodium phosphate buffer solution (pH 7.2) containing 50% propylene glycol was allowed to flow through the column at a flow rate of 5 ml/min to remove impurity proteins, followed by washing with about 3 CV of an equilibration buffer solution. Then, about 3 CV of 20 mM sodium phosphate buffer solution (pH 7.2) containing 2M NaCl was allowed to flow through the column at a flow rate of 5 ml/min to remove impurity proteins. Finally, about 3 CV of 20 mM sodium phosphate buffer solution (pH 7.2) containing 2M NaCl and 20% propylene glycol was allowed to flow through the column at a flow rate of 5 ml/min to remove impurity proteins.

Figure 2:
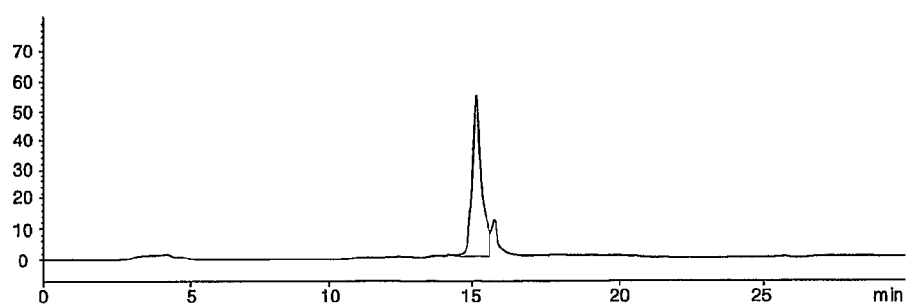
FIG. 2 is a C4 RP-HPLC (Reversed-Phase High-Performance Liquid Chromatography) analysis chromatogram of interferon beta eluted in affinity chromatography according to a purification process of the present invention.

About 3 CV of an elution buffer solution (20 mM sodium phosphate buffer solution containing 2M NaCl and 50% propylene glycol, pH 7.2) was allowed to flow through the column at a flow rate of 5 ml/min to thereby recover an interferon beta-containing solution. The purity of the eluted solution thus recovered was measured using C4 HPLC analysis chromatography and the result is shown in FIG. 2. Referring to FIG. 2, the purity of interferon beta was about 85% or more.

Figure 3:
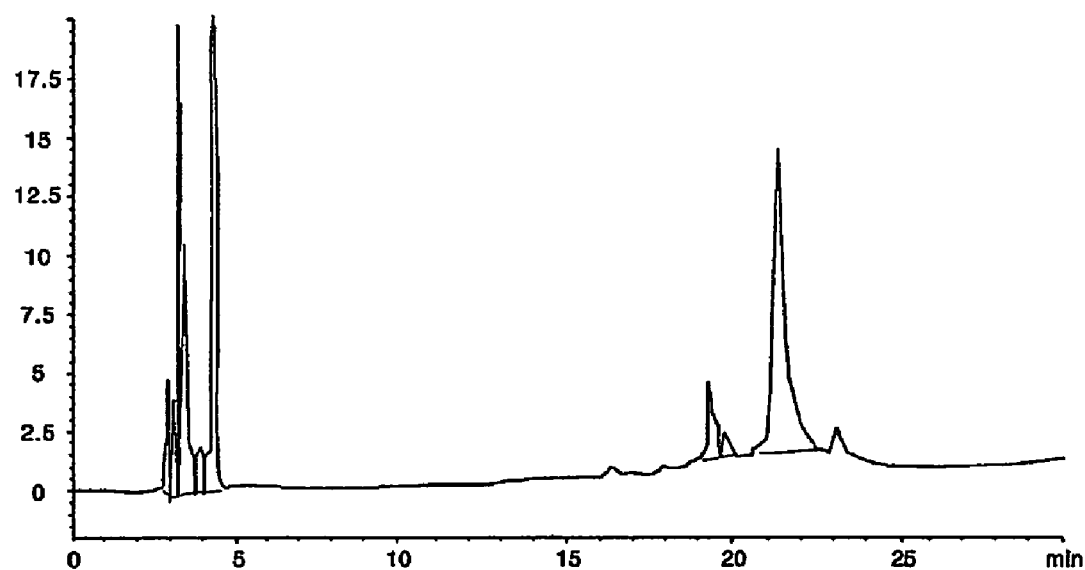
FIG. 3 is C4 RP-HPLC analysis chromatogram of interferon beta eluted without washing with 50% propylene glycol.

As a control, affinity chromatography was performed according to the above-described manner except that washing with a 20 mM sodium phosphate buffer solution (pH 7.2) containing 50% propylene glycol was omitted. The purity of the resultant eluted solution was measured using C4 HPLC analysis chromatography and the result is shown in FIG. 3. It can be seen from FIG. 3 that the absence of the washing with 20 mM sodium phosphate buffer solution (pH 7.2) containing 50% propylene glycol remarkably decreases the purity of interferon beta.

Example 2

Cation Exchange Chromatography

The interferon beta-containing solution obtained according to the present invention in Example 1 underwent diafiltration using an ultrafiltration system (molecular weight cut-off of 10,000) and then was loaded on a CM-Sepharose FF (Amersham biosciences, Sweden) column (XK-50, 150 ml CV, Amersham biosciences, Sweden) at a flow rate of 1.5 ml/min. The column was then equilibrated with about 3 CV of a 50 mM sodium phosphate buffer solution (pH 6.7) at a flow rate of 5 ml/min. Elution of interferon beta was performed by a linear concentration gradient from a 50 mM sodium phosphate buffer solution (pH 6.7) to a 50 mM sodium phosphate buffer solution (pH 6.7) containing 400 mM NaCl to thereby recover sugar chain-linked interferon beta fractions.

Example 3

Gel-Filtration Chromatography

An interferon beta-containing solution obtained in Example 2 was concentrated to 200 μg/ml and was replaced 500 times or more by a 20 mM sodium acetate buffer solution (pH 4.0). The resultant solution was loaded on a Sephacryl S-200 column (1700 ml, XK-50/100, Amersham biosciences, Sweden) equilibrated with a 20 mM sodium acetate buffer solution (pH 4.0) to obtain an interferon beta-containing solution.

Example 4

Reversed-Phase High-Performance Liquid Chromatography (RP-HPLC) Analysis

Each solution obtained in Examples 1, 2, and 3 was loaded on a C4 RP-HPLC column (Vydac 214TP54, 4.6 mm in inner diameter×25 cm in length, 5 μm in particle size, 300 Å in pore size) at a flow rate of 1 ml/min. Then, 20 CV of a 0.1% trifluoroacetic acid-containing acetonitrile was allowed to flow through the column by a linear concentration gradient from 30% acetonitrile containing 0.1% trifluoroacetic acid to 80% acetonitrile containing 0.1% trifluoroacetic acid, to analyze chromatogram patterns.

Figure 4:
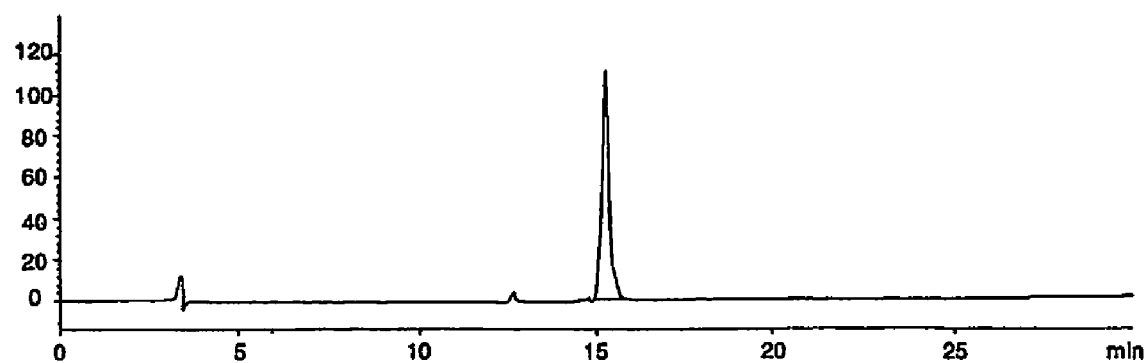
FIG. 4 is a C4 RP-HPLC analysis chromatogram of an eluted solution after gel-filtration.

An analysis result after the gel-filtration chromatography is shown in FIG. 4. From FIG. 4, it can be seen that the present invention can produce a high purity interferon beta.

According to a purification process of the present invention, interferon beta can be purified with high purity of 99% or more using nontoxic propylene glycol and enhanced affinity chromatography.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A process for purifying human interferon beta from a recombinant human interferon beta-containing culture comprising performing affinity chromatography and cation exchange chromatography, wherein the affinity chromatography comprises:

adsorbing the interferon beta-containing culture to an equilibrated affinity chromatography column, followed by washing with an equilibration buffer solution;

followed by washing the column with a first washing buffer solution A of pH 6.5-7.5 containing 30-60 wt % of propylene glycol;

followed by washing the column with a second washing buffer solution C of pH 6.5-7.5 containing 1-2M NaCl;

followed by washing the column with a third washing buffer solution B of pH 6.5-7.5 containing 10-30 wt % propylene glycol and 1-2M NaCl; and then eluting a human interferon beta-containing fraction with a buffer solution of pH 6.5-7.5 containing 40-60 wt % propylene glycol and 1-2M NaCl.

2. The process of claim 1, wherein each buffer solution used in the washing and the elution is a sodium phosphate buffer solution or a potassium phosphate buffer solution.

3. The process of claim 1, wherein a solution obtained by the affinity chromatography, before the cation exchange chromatography, is subjected to diafiltration with an ultrafiltration membrane with a molecular weight cut-off of 10,000 daltons.

4. The process of claim 3, wherein in the cation exchange chromatography, a sample obtained by the diafiltration is loaded on a column and then a human interferon beta-containing fraction is eluted at pH 5-7 by a concentration gradient of NaCl.

* * * * *